(12) United States Patent
Graczyk

(10) Patent No.: US 6,684,885 B2
(45) Date of Patent: Feb. 3, 2004

(54) LASER SURGERY EYE SHIELD

(76) Inventor: Paul M. Graczyk, 61 Brookside Dr., Glendale Heights, IL (US) 60139

( * ) Notice: Subject to any disclaimer, the term of this patent is extended or adjusted under 35 U.S.C. 154(b) by 0 days.

(21) Appl. No.: 10/083,043

(22) Filed: Feb. 26, 2002

(65) Prior Publication Data

US 2002/0078965 A1 Jun. 27, 2002

Related U.S. Application Data

(63) Continuation-in-part of application No. 09/336,879, filed on Jun. 18, 1999, now Pat. No. 6,349,726.

(51) Int. Cl.[7] .................................................. A61F 9/00
(52) U.S. Cl. ........................................................ 128/858
(58) Field of Search ................................ 128/858, 853; 606/1, 5, 10

(56) References Cited

U.S. PATENT DOCUMENTS

| 3,074,407 | A | * | 1/1963 | Moon et al. ............... 606/166 |
|---|---|---|---|---|
| 4,653,495 | A | * | 3/1987 | Nanaumi ..................... 606/10 |
| 4,688,570 | A | * | 8/1987 | Kramer et al. .............. 606/166 |
| 4,739,761 | A | * | 4/1988 | Grandon ..................... 606/166 |
| 4,903,695 | A | * | 2/1990 | Warner et al. ................ 606/5 |
| 5,163,934 | A | * | 11/1992 | Munnerlyn ................... 606/5 |
| 5,312,428 | A | * | 5/1994 | Lieberman ................. 606/166 |
| 5,368,590 | A | * | 11/1994 | Itoh ............................. 606/5 |
| 5,505,723 | A | * | 4/1996 | Muller ......................... 606/5 |
| 5,616,139 | A | * | 4/1997 | Okamoto ..................... 606/4 |
| 5,772,675 | A | * | 6/1998 | Hellenkamp .............. 606/166 |
| 5,807,380 | A | * | 9/1998 | Dishler ........................ 606/5 |
| 5,833,701 | A | * | 11/1998 | Gordon ..................... 606/166 |
| 6,349,726 | B1 | * | 2/2002 | Graczyk .................... 128/858 |

* cited by examiner

Primary Examiner—David M. Shay
(74) Attorney, Agent, or Firm—Robert L. Marsh

(57) ABSTRACT

A transparent flexible shield is provided to protect the outer portions of the cornea and the under surface of a cap of the cornea during LASIK surgery comprising a transparent annular body with a central opening. The central opening is sized to be a little smaller than the outer diameter of the cut made to form the cap. The shield is positioned on the upper surface of the cornea and the folded cap to protect the outer edges thereof from exposure to the ray of the laser.

8 Claims, 2 Drawing Sheets

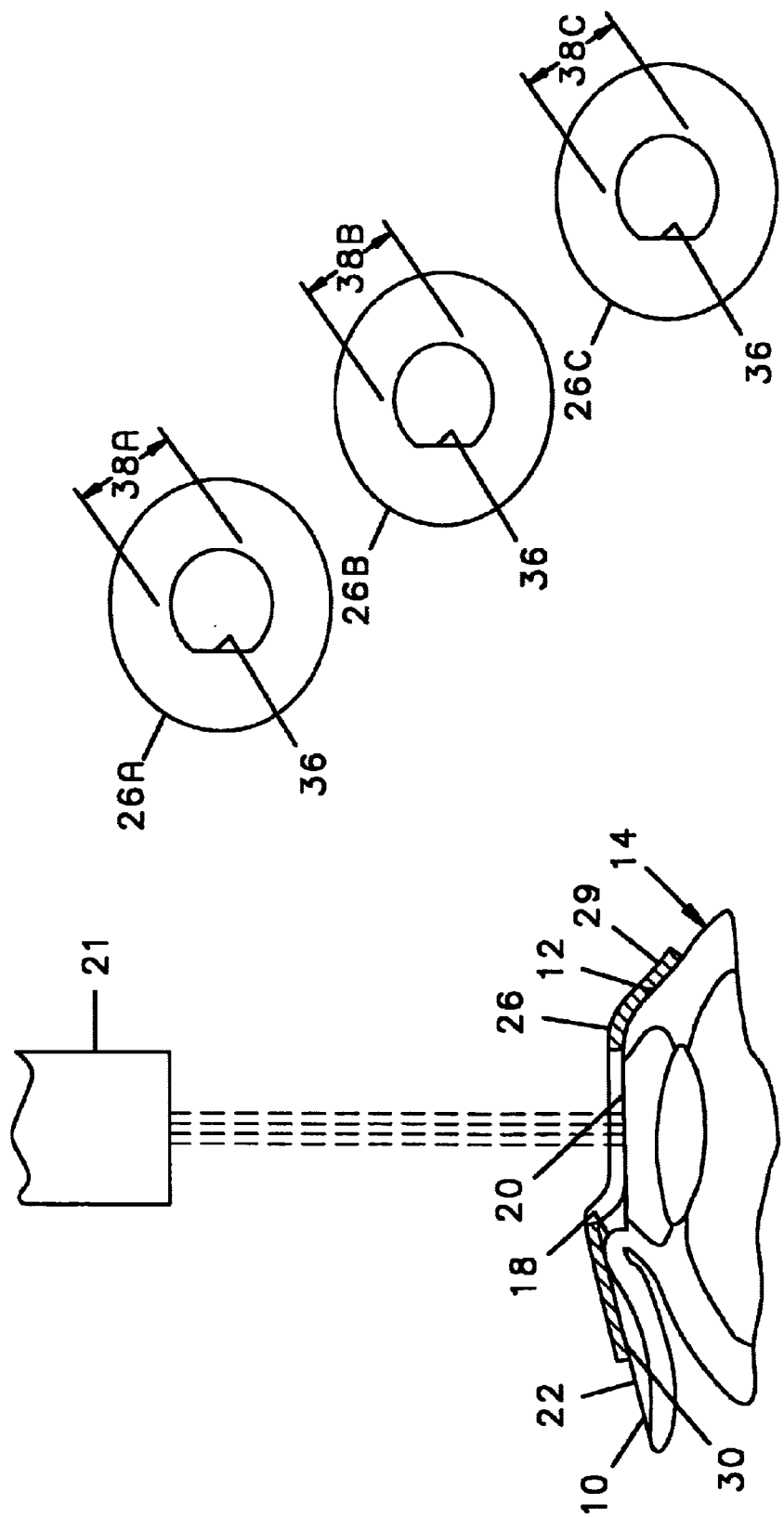

US 6,684,885 B2

LASER SURGERY EYE SHIELD

This is a continuation-in-part of my application filed Jun. 18, 1998 and assigned Ser. No. 09/336,879, now U.S. Pat. No. 6,349,726. The present invention relates to laser surgery for correcting myopia and hyperopia and in particular to a shield to protect the peripheral portions of the cornea from the laser during the course of such surgery.

BACKGROUND OF THE INVENTION

Laser surgery can be used to remove portions of the cornea of the eye thereby reshaping the cornea to correct myopia and hyperopia. During such surgery, a portion of the cornea is removed by the laser thereby reshaping the surface of the cornea to change the focal length of the lens to compensation for the effects of myopia and hyperopia.

To undertake such surgery, it is desirable to remove the upper surface of the cornea such that the lower portion of the cornea is exposed to the laser during surgery. After the laser has reshaped a lower portion of the cornea, the upper surface is replaced and eye is allowed to heal.

A preferred procedure known as Laser Assisted Interastromal Keratomileusis, commonly known as "LASIK", involves the cutting of a dome shaped cap from the cornea with a portion of the cap still attached to the cornea to form a hinge. The cap is then folded backwards to expose a lower portion of a cornea. The laser is then used to reshape the lower portion of the cornea, and after the lower portion has been reshaped the cap is repositioned and allowed to heal. The procedure is described in Dishler U.S. Pat. No. 5,807,380. The surgery is carried out by a pre-programmed computerized laser controlled by the surgeon who must be able to see the surface of the eye during the surgery.

During LASIK surgery, the laser beam should be directed at only the lower portion of the cornea exposed after removal of the cap, and it is undesirable for the laser to strike the peripheral edge of the opening formed when the cap has been removed or the fold which constitutes the hinge allowing the cap to be folded backward. It would, therefore, be desirable to provide an improved method and apparatus for protecting the vulnerable portions of the cornea from damage by the laser during laser surgery. It is also be desirable that the apparatus obstruct as little as possible of the surgeon's vision during the surgery.

SUMMARY OF THE INVENTION

Briefly, the present involves an apparatus and a method of performing laser eye surgery comprising the steps of cutting a cap a material from the outer surface of the cornea of the eye to form a flap having given outer dimensions and a joined edge forming a hinge. The cap is then folded backwards along the joined edge to expose the lower portion of the cornea which is to be re-contoured by the beam of a laser.

In accordance with the invention, an annular shield is provided having a central opening with dimensions which do not exceed the given dimensions of the perimeter of the cap and having a concave lower surface which is complimentary to the shape of the outer surface of an eye. Preferably, a plurality of such shields are provided, with each of such shields having a different sized central opening such that a shield having a central opening sized to best fit the size of the lower portion of the cornea under the cap can be selected for use with the eye undergoing surgery.

The annular shield is positioned with the lower surface thereof upon the portion of the eye surrounding the cut forming the cap and over the folded flap with the lower portion of the cornea exposed through the central opening. Thereafter, the laser beam is directed through the central opening to perform the surgery. When the shield is made of a rigid material, the shield's lower surface is concave and complementary in shape to the outer surface of the eye.

In accordance with one embodiment of the invention the shield is made of a flexible and transparent material. Flexibility allows the shield to conform to the shape of the eye and to thereby rest comfortably on the upper surface of the eye and thereby not cause injury to the eye. Flexibility also permits a portion of the shield to rest on the upper surface of the eye while a another portion thereof rests on the fold of the cap. The transparent shield creates minimal obstruction to the physician's view of the eye during the surgery.

In the preferred embodiment, the central opening comprises an arc of approximately 270 degrees of a circle and the remaining 90 degrees is a cord connecting the distal ends of the partial circle. Since the shape of each patient's eye is different, a plurality of shields, each with a different sized central opening, are provided such that a shield having the central opening suitable for use during the surgery of any eye shape is available for use.

BRIEF DESCRIPTION OF THE DRAWINGS

A better understanding of the present invention will be had after a reading of the following detailed description taken in conjunction with the drawings wherein:

FIG. 3 is a cross sectional view of the shield shown in FIG. 2 resting on the surface of an eye having a cap removed as shown in FIG. 1;

FIG. 4 is a front elevational view of a set of three shields of the type shown in FIG. 2, each with the central opening of each defining a different central diameter.

DETAILED DESCRIPTION OF THE PREFERRED EMBODIMENT

Figure 2:
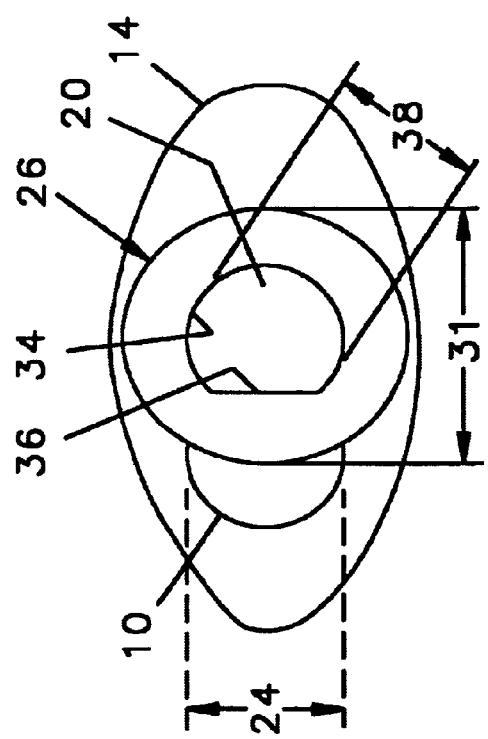
FIG. 2 is a front elevational view of a shield in accordance with the present invention fitted over an eye having a flap folded backwards and the lower portions of the cornea visible through the central opening of the shield.
Figure 1:
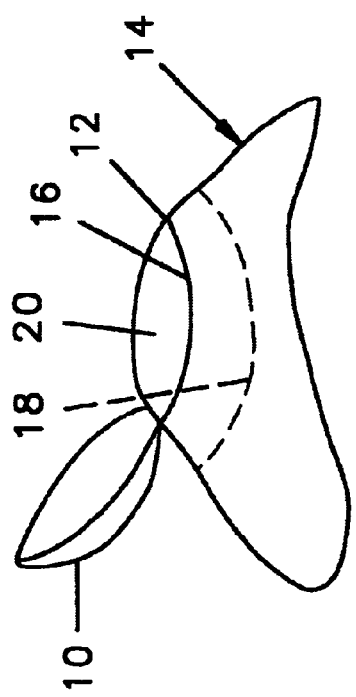
FIG. 1 is a fragmentary isometric view of an eye having a cap removed from the upper surface of the cornea to expose a lower portion thereof.

Referring to FIGS. 1 to 3, in accordance with the LASIK procedure, a dome shaped cap 10 is removed from the cornea 12 of an eye 14 by making a semi-circular peripheral cut 16 which does not close to a circle as shown. The uncut portion 18 serves as a hinge to permit the cap 10 to be folded away from the center of the cornea and leave exposed a lower layer 20 the cornea. In accordance with the LASIK procedure, the upper surface of the lower layer 20 is reshaped by subjecting the cornea to a precision operated laser 21.

It is desirable to apply the laser 21 to the lower layer 20 without subjecting any of the upper surface of the cornea 12 which surrounds the cut 16, or the under surface 22 of the cap 10 to the rays thereof A complicating factor in the problem of protecting the surrounding cornea and the under surface 22 of the cap is that there are minor differences between the shapes of the eyes of patients, and, as a result thereof, the outer diameter 24 to the cap 10 is different from one patient to another. Another complicating problem is that when the cap 10 is folded backwards, as shown in FIG. 3, the uncut portion 18 or hinge of the cap and the cap 10 itself create an elevated mass on the outer surface of the eye 14 which will prevent a shield having a rigid semi-spherical lower surface from resting with its weight thereof applied evenly on the underlying surface. In fact, a rigid shield with a semi-spherical lower surface will rest at an angle such that portions of the shield will be spaced from the surface of the eye, thereby reducing the effectiveness of the shield to obstruct the undesired rays of the laser. A third complicating factor is that a shield made of a non-material such as metal will necessarily obstruct the physician's view of the surgery being performed.

In accordance with the present invention, to protect the portion of the outer surface of the cornea 12 which surrounds the cut 16 and the under surface 22 of the cap 10, a shield 26 in accordance with the present invention is provided. The shield 26 is generally annual in shape, having a circular outer peripheral edge 28, and having generally planar upper and lower surfaces 29, 30 respectively.

There are no fixed requirements for the outer diameter 31 of a shield, but typically, the outer diameter 31 may be approximately 16.5 mm. The inner opening of the shield includes a semi circular arc portion 34 which defines approximately 270 degrees of a circle, and connecting the ends of the semi-circular arc portion is a cord 36 which defines the remaining 90 degrees of the central opening.

An important feature of the invention is that the shield 26 is made of a flexible and transparent material. Since the shield 26 is flexible the weight thereof will generally be applied evenly across the underlying surface of the eye 14 and the entire lower surface 30 of the shield 10 will abut either the upper surface of the eye 14 or the lower surface 22 of the cap 10 as shown in FIG. 3. The effectiveness of the shield is therefore maximized because the edge of the inner opening 34, 36 lies against the surfaces to be protected. Also, the shield 26 will cause a minimum of obstruction to the physician's view of the surgery because it is made of a transparent material.

It should be appreciated that the rays of a laser will only penetrate a flexible transparent material to a very shallow depth and therefor the transparent qualities do not compromise the effectiveness of the shield 26 to protect portions of the eye from the rays of the laser 21. The material is effectively opaque to the laser rays.

Referring to FIG. 4, it is desirable to provide a plurality of shields 26A, 26B, 26C in a set 40 with each shield having a central opening defining a different diameter 38A, 38B, 38C. The surgeon can then select a shield from the set 40 which has an inner diameter 38 suitable for use on the eye of a patient who is to receive eye surgery using the LASIK procedure. Preferably, the inner diameters 38 of a semicircular portion 34 of a set of shields should range from a minimum of 0.50 mm to a maximum of 15.0 mm, with successive shields having a difference in diameter of approximately 0.50 mm.

When a suitably sized shield 26 is positioned over the center of the cornea 12, with the cord 36 positioned along the fold of the uncut portion 18, only the lower layer 20 can be seen through the central opening thereof. The edge of the cut 16, the portion of the cornea 12 surrounding the cut 16, and the under surface 22 of the cap 10 are all visible through the transparent shield 26 and are protected by the shield from the rays of the laser directed at the cornea of the eye.

If the shield 26 is to be made of a rigid material the lower surface 30 is preferably concave in shape to conform to the shape of the eye and is polished so as not to cause irritation to the surface of the eye. It should also be apparent that the body of the shield 26 is made of a suitable material which can withstand and absorb the energy of the laser 21 without conducting excess heat to the surrounding eye.

While the present invention has been disclosed with respect to a single embodiment, it will be appreciated that many variations and modifications can be made without departing from the true spirit and scope of the present invention. Therefore, it is the intent of the following claims to cover all such modifications and variations which fall within the true spirit and scope of the invention.

What is claimed:

1. A shield for use with a laser in surgery on the cornea of an eye wherein a cap with periphery a portion of which is a semi-circular arc defining a diameter is cut from an upper portion of said cornea, leaving an uncut portion for retaining said cap to said eye, said uncut portion defining a cord joining ends of said semi-circular arc, said cap folded away from an underlying lower portion of said cornea, said fold being along said uncut portion to expose a lower surface of said cornea, said shield comprising a transparent annular body having a lower surface and a central opening defining an inner edge, said transparent body being opaque to rays of said laser, said central opening having a semi-circular portion defining a diameter no greater than said diameter defined by said semi-circular arc of said cap and a cord portion joining ends of said semi-circular portion, said transparent body positionable on said eye with said semi-circular portion protecting a portion of said eye surrounding said cut and said cord positionable for protecting said uncut portion of said cap wherein said shield leaves only said lower surface of said cornea exposed to said laser.

2. A plurality of shields in accordance with claim 1 wherein each of said shields has a different inner diameter, each of said shields for use with a cap having a different outer diameter.

3. A shield in accordance with claim 1 wherein said transparent body is made of a flexible material.

4. The method of performing eye surgery comprising the steps of:

a surgeon cutting a layer of material from the outer surface of the cornea of an eye to form a cap having a semi-circular periphery, said semi-circular periphery defining a given diameter, said cap joined to said cornea by an uncut portion forming a cord joining ends of said semi-circular periphery, said uncut portion serving as a hinge, folding said cap along said uncut portion to expose a lower portion of said cornea, said lower portion having a perimeter with a semi-circular portion complimentary to said semi-circular portion of said cap and a having a cord joining ends of said semi-circular portion equal in length to said uncut portion of said cap, providing an annular shield having a transparent body, a lower surface and a central opening defining a diameter which is not greater than said given diameter, positioning said annular shield on said eye and over said hinge with said lower surface contacting an upper surface of said cornea, and said lower portion of said cornea being visible through said central opening of said shield and said upper portion of said cornea below said annular shield being visible through said transparent body of said shield, directing a laser beam through said central opening to perform said surgery, and said surgeon watching said surgery through said transparent shield.

5. The method in accordance with claim 4 wherein said central opening of said shield comprises a semi-circular portion and a cord joining distal ends of said semi-circular portion, said cord being equal in length to said uncut portion of said cap, and positioning said cord of said central opening of said shield over said uncut portion of said cap and positioning said semi-circular portion over portions of the eye surrounding said semi-circular portion of said perimeter of said exposed lower portion of said eye to provide protection during surgery.

6. The method of claim 4 wherein said shield is made of a flexible material.

7. The method of claim 6 wherein said central opening of said shield comprises a semi-circular portion and a cord joining distal ends of said semi-circular portion, said cord being equal in length to said uncut portion of said cap, and positioning said cord of said central opening of said shield over said uncut portion of said cap and positioning said semi-circular portion over portions of the eye surrounding said semi-circular portion of said perimeter of said exposed lower portion of said eye to provide protection during surgery.

8. The method of claim 4 and further comprising the step of selecting said shield from a plurality of shields, where each of said plurality of shields has a different defined diameter of said central opening, and said defined diameter of said selected shield is no greater than said given diameter.

* * * * *